(12) United States Patent
Brown et al.

(10) Patent No.: US 7,582,118 B2
(45) Date of Patent: Sep. 1, 2009

(54) FEMORAL TROCHLEA PROSTHESES

(75) Inventors: Jeffrey D. Brown, Warsaw, IN (US);
Adam M. Griner, Columbia City, IN (US); Robert A. Hodorek, Warsaw, IN (US); Raymond C. Parisi, Wakarusa, IN (US); Brian E. Vanskyock, Fort Wayne, IN (US); Justin J. May, Leesburg, IN (US); James C. Harris, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

(21) Appl. No.: 11/671,643

(22) Filed: Feb. 6, 2007

(65) Prior Publication Data

US 2008/0188942 A1    Aug. 7, 2008

(51) Int. Cl.
*A61F 2/38* (2006.01)
(52) U.S. Cl. .................. 623/20.36; 623/20.17; 623/20.3
(58) Field of Classification Search .............. 623/20.14, 623/20.15, 20.18, 20.19, 20.35, 20.36
See application file for complete search history.

(56) References Cited

U.S. PATENT DOCUMENTS

| 5,702,459 | A | 12/1997 | Hummer et al. |
| 6,190,415 | B1 | 2/2001 | Cooke et al. |
| 6,797,006 | B2 * | 9/2004 | Hodorek ................. 623/20.36 |
| 7,172,597 | B2 * | 2/2007 | Sanford ........................ 606/88 |
| 2004/0236428 | A1 | 11/2004 | Burkinshaw et al. |
| 2007/0123992 | A1 * | 5/2007 | Sanford ................. 623/20.35 |
| 2008/0188855 | A1 | 8/2008 | Brown et al. |

FOREIGN PATENT DOCUMENTS

| FR | 2521421 A1 | 8/1983 |
| FR | 2594323 A1 | 8/1987 |
| FR | 2682589 A1 | 4/1993 |
| FR | 2740325 A1 | 4/1997 |
| WO | WO03/068119 A2 | 8/2003 |

OTHER PUBLICATIONS

The European Search Report mailed May 27, 2008, in related European application No. EP08250442.4.
The European Search Report mailed May 5, 2008, in European application No. EP08250441.6.

* cited by examiner

*Primary Examiner*—David Isabella
*Assistant Examiner*—Yashita Sharma
(74) *Attorney, Agent, or Firm*—Baker & Daniels LLP

(57) ABSTRACT

Various embodiments of femoral trochlea prostheses useable in a knee joint. The knee joint includes a patella and a distal femur with a femoral trochlea, or patello-femoral groove. In one embodiment, a femoral trochlea prosthesis includes a distal tail. In another embodiment, a femoral trochlea prosthesis includes a wing or extension portion. In yet another embodiment, a set of femoral trochlea prostheses includes a plurality of prostheses having differing thicknesses. In still another embodiment, a femoral trochlea prosthesis includes a porous medium on various portions of the prosthesis.

13 Claims, 3 Drawing Sheets

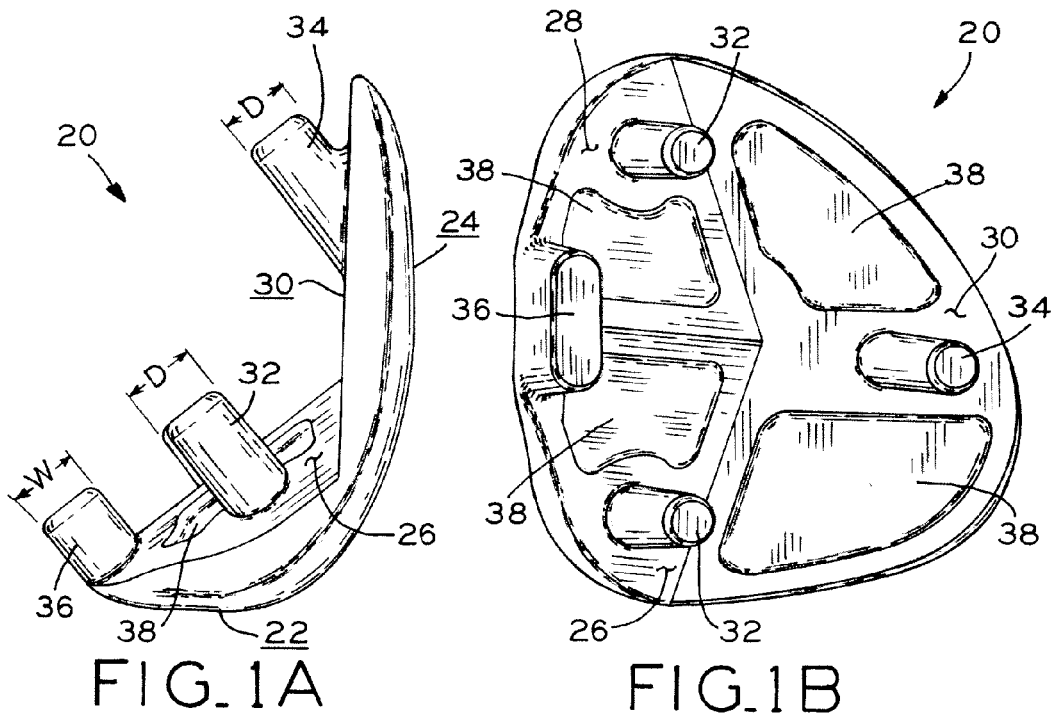
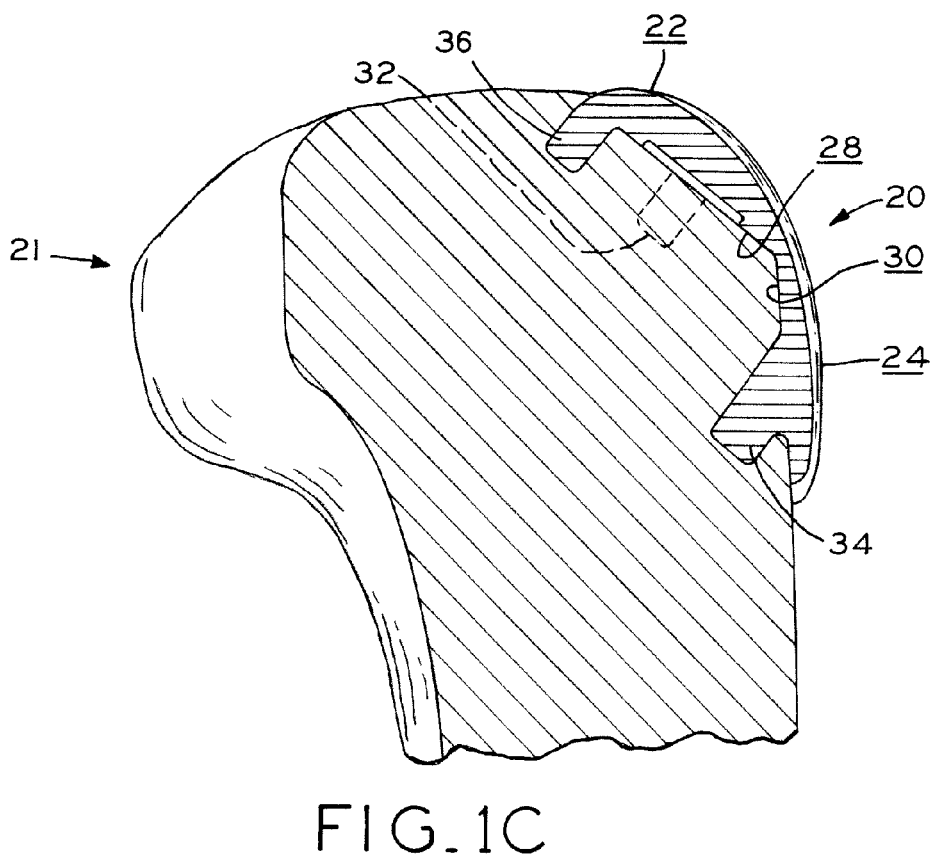

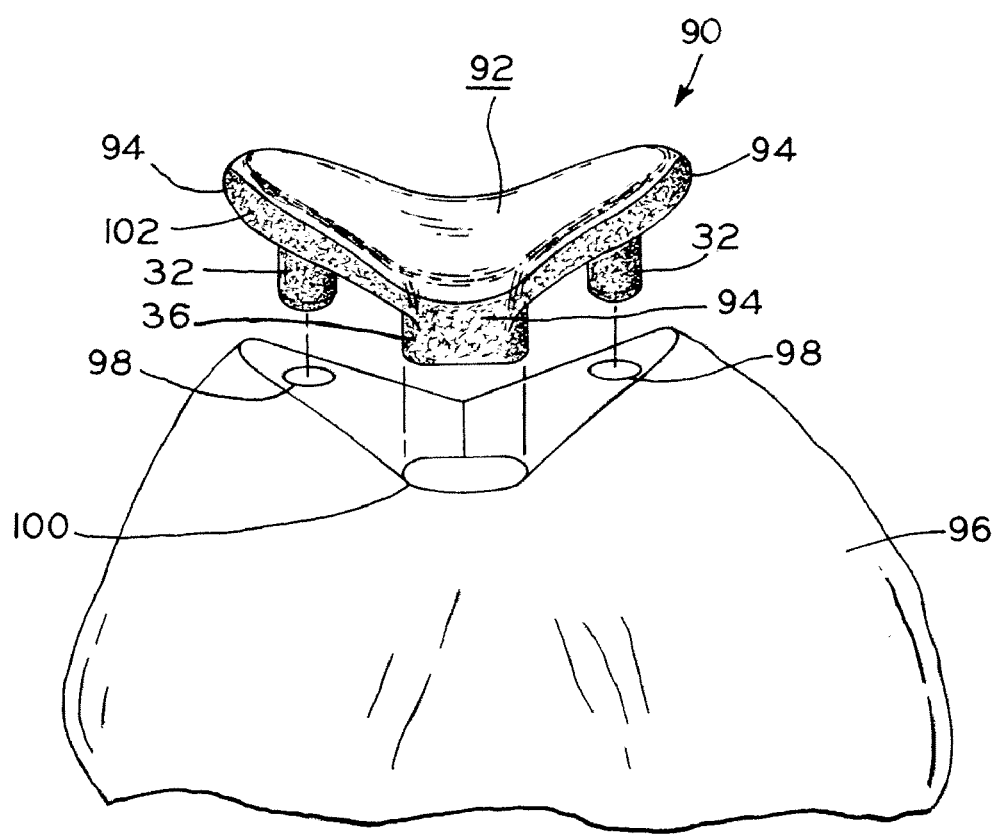
FIG_4

FEMORAL TROCHLEA PROSTHESES

BACKGROUND

1. Field of the Invention

The present invention relates to knee joint prostheses. More particularly, the present invention relates to various embodiments of exemplary femoral trochlea prostheses.

2. Description of the Related Art

Disease and trauma affecting the patello-femoral joint of a knee are commonly treated by surgically replacing the femoral trochlea with femoral trochlea implants or prostheses according to a procedure known as a patello-femoral joint (PFJ) replacement. Although femoral trochlea prostheses are provided in a range of varying sizes and are selected by surgeons to best fit the anatomy of a particular patient, improvements in the design of femoral trochlea prostheses are desired.

SUMMARY

The present disclosure provides various embodiments of femoral trochlea prostheses useable in a knee joint. The knee joint includes a patella and a distal femur with a femoral trochlea, or patello-femoral groove. In one embodiment, a femoral trochlea prosthesis includes a distal tail. In another embodiment, a femoral trochlea prosthesis includes a wing or extension portion. In yet another embodiment, a set of femoral trochlea prostheses includes a plurality of prostheses having differing thicknesses. In still another embodiment, a femoral trochlea prosthesis includes a porous medium on various portions of the prosthesis.

In one form thereof, the present disclosure provides a femoral trochlea prosthesis for implantation in a distal femur of a knee joint, the prosthesis articulating with a patellar component of the knee joint, the prosthesis including an articulating surface; a nonarticulating surface, the nonarticulating surface defining at least one anterior nonarticulating surface and at least one distal nonarticulating surface; and at least one fixation support extending from the nonarticulating surface proximate a distal most region of the prosthesis, the fixation support extending in a direction noncoplanar with the anterior nonarticulating surface, the articulating surface transitioning smoothly into the fixation support.

In another form thereof, the present disclosure provides a femoral trochlea prosthesis for implantation in a distal femur of a knee joint, the prosthesis articulating with a patellar component of the knee joint, including an articulating surface; a nonarticulating surface; and means for fixating the prosthesis in the distal femur and for facilitating articulation of the prosthesis against the patellar component when the knee joint transitions between flexion and extension.

In yet another form thereof, the present disclosure provides a femoral trochlea prosthesis for implantation in a distal femur of a knee joint, including an articulating surface; a nonarticulating surface; and a bone engaging extension portion extending from the nonarticulating surface and defining a space between at a least a portion of the nonarticulating surface and the distal femur.

In a still further form thereof, the present disclosure provides a femoral trochlea prosthesis for implantation in a distal femur of a knee joint, including an articulating surface; a nonarticulating surface; and extension means for defining a space between the nonarticulating surface and the distal femur and for supporting the prosthesis on the distal femur.

In another form thereof, the present disclosure provides a set of femoral trochlea prostheses, including a first femoral trochlea prosthesis, including a first articulating surface comprising at least a first distal articulating surface and a first anterior articulating surface; and a nonarticulating surface comprising at least a first anterior nonarticulating surface and at least at a first distal nonarticulating surface; the first distal articulating surface and the first distal nonarticulating surface defining a first distal thickness; the first anterior articulating surface and the first anterior nonarticulating surface defining a first anterior thickness; a second femoral trochlea prosthesis, including a second articulating surface comprising at least a second distal articulating surface and a second anterior articulating surface; and a second nonarticulating surface comprising at least a second anterior nonarticulating surface and at least a second distal nonarticulating surface; the second distal articulating surface and the second distal nonarticulating surface defining a second distal thickness; the second anterior articulating surface and the second anterior nonarticulating surface defining a second anterior thickness; the first distal thickness greater than the second distal thickness; and the first anterior thickness substantially equal to the second anterior thickness.

In yet another form thereof, the present disclosure provides a prosthesis including an articulating surface, the articulating surface defining a perimeter of the prosthesis, at least a portion of the perimeter being formed of a porous material.

BRIEF DESCRIPTION OF THE DRAWINGS

The above-mentioned and other features of this disclosure, and the manner of attaining them, will become more apparent and will be better understood by reference to the following description of embodiments of the disclosure taken in conjunction with the accompanying drawings, wherein:

FIG. 1A is a side view of an exemplary femoral trochlea prosthesis according to one embodiment of the present disclosure;

FIG. 1B is a backside or nonarticulating side view of the prosthesis of FIG. 1A;

FIG. 1C is a cross-sectional view of the prosthesis of FIG. 1A, further illustrating a portion of a distal femur in which the prosthesis is implanted;

FIG. 4 is an exploded perspective view of an exemplary femoral trochlea prosthesis according to still another embodiment of the present disclosure.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 2:
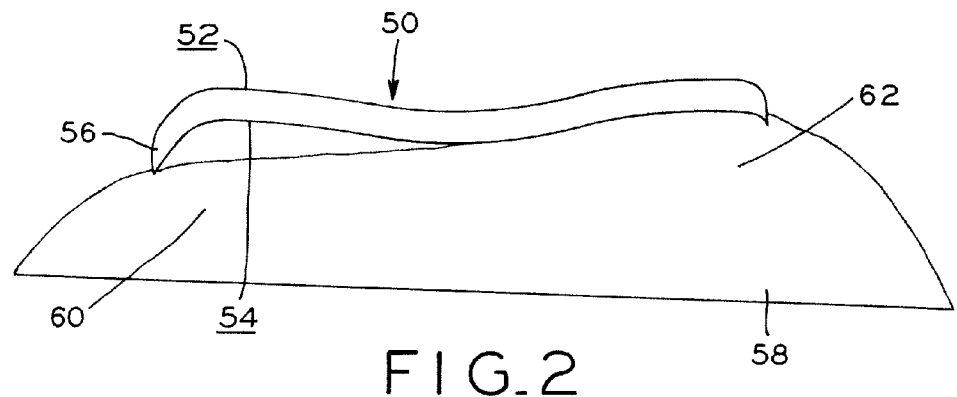
FIG. 2 is a proximal view of an exemplary femoral trochlea prosthesis according to another embodiment of the present disclosure.

The present disclosure provides various embodiments of femoral trochlea prostheses useable in a knee joint. The prostheses described herein may be useable in a knee joint in which a patella is resurfaced or a knee joint in which a patella is not resurfaced. The prostheses described herein may be secured to a femur with cement or, alternatively, without cement, such as with fixation pegs, a porous medium such as a material made using Trabecular Metal™ technology or Cancellous-Structured Titanium™ (CSTi™) technology, both available from Zimmer, Inc. of Warsaw, Ind., screws and/or cables, for example. The prostheses described herein may be formed of metal, polymer, or hydrogel. Moreover, due to the relatively small thicknesses of the prostheses described herein, the prostheses do not violate a primary total knee arthroplasty (TKA) envelope, i.e., minor or no adjustments of the primary TKA technique are required to revise a failed patello-femoral joint to a TKA.

All of the prostheses described herein may incorporate various features and be useable in systems using the techniques and methods described in co-pending U.S. patent application entitled FEMORAL TROCHLEA PROSTHESES, (hereinafter "the Co-Pending application"), filed on the same day as the present application and assigned to the assignee of the present application, the disclosure of which is expressly incorporated herein by reference.

Referring to FIGS. 1A, 1B, and 1C, femoral trochlea prosthesis 20 may include distal articulating surface 22, anterior articulating surface 24, and a plurality of nonarticulating surfaces. First distal nonarticulating surface 26, second distal nonarticulating surface 28, and anterior nonarticulating surface 30 are positionable against a resected patello-femoral joint, or femoral trochlea, of femur 21. Articulating surfaces 22 and 24 may articulate against a resurfaced or unresurfaced patella (not shown). In an exemplary embodiment, as shown in FIG. 1C, distal articulating surface 22 may be shaped such that a sagittal profile of prosthesis 20 substantially matches the anatomy of femur 21. Due to the inlayed nature of prosthesis 20, a smooth transition between cartilage and prosthesis 20 is provided to facilitate a smooth articulation with the patella.

Prosthesis 20 may include a plurality of pegs to facilitate securement in femur 21 and support of prosthesis 20. Anterior bone peg 34 may extend from anterior nonarticulating surface 30. Distal bone pegs 32 may extend from distal nonarticulating surfaces 26 and 28.

Prosthesis 20 may also include distal tail 36 extending from distal nonarticulating surfaces 26 and 28. Distal tail 36 may be positioned at a point located most posteriorly on prosthesis 20 and may medially/laterally extend across at least a portion of distal nonarticulating surfaces 26 and 28. Distal tail 36 extends a sufficient distance from surfaces 26 and 28 such that, when implanted in femur 21, distal tail 36 may provide additional fixation support between prosthesis 20 and femur 21. Furthermore, distal tail 36 may provide additional support for the patella in flexion and protects against a non-smooth, patella transition from flexion to extension, e.g., distal tail 36 facilitates prevention of patella catching. Prevention of patella catching facilitates use of prosthesis 20 in a variety of different anatomies. Distal tail 36 also may facilitate strengthening and/or stiffening of prosthesis 20, particularly in a region of prosthesis 20 experiencing high patellar loads, thereby enhancing the longevity of prosthesis 20. Moreover, distal tail 36 facilitates prevention of liftoff micromotion of prosthesis 20 because of the abutting relationship between distal tail 36 and femur 21.

In an exemplary embodiment, distal tail 36 extends substantially perpendicular, i.e., approximately at an angle of 90°, to distal nonarticulating surfaces 26 and 28, as shown in FIG. 1A. Distal tail 36 may extend at an angle to distal nonarticulating surfaces 26 and 28 as small as approximately 65°, 75°, or 85°, or as large as approximately 95°, 105°, or 115°. Distal bone pegs 32 and anterior bone peg 34 may also extend in directions substantially parallel to each other and to the extension direction of distal tail 36 to facilitate bone preparation and insertion of prosthesis 20. In an exemplary embodiment, distal tail 36 has width W which is substantially equal to diameter D of bone pegs 32 and 34. In this manner, a drill used to prepare femur 21 to receive bone pegs 32 and 34 may also be used to prepare femur 21 to receive distal tail 36. For example, the drill may first drill holes in femur 21 for receipt of bone pegs 32 and 34 and then drill a plurality of holes in femur 21 in a side-by-side manner to form a cavity for receipt of distal tail 36. The drill could alternatively be used in a router-type manner to form a cavity for receipt of distal tail 36. Such use of the same drill to form cavities in femur 21 for receipt of bone pegs 32, 34 and distal tail 36 facilitates a surgical procedure and eliminates the need for an additional surgical instrument used to form the cavity for distal tail 36. However, diameter D of bone pegs 32, 34 and width W of distal tail 36 may also be different values. In one embodiment, bone pegs 32, 34 and distal tail 36 extend an equal distance above their respective nonarticulating surfaces of prosthesis 20 to further facilitate bone preparation for receipt of prosthesis 20. In another embodiment, bone pegs 32, 34 and distal tail 36 extend unequally with respect to each other above their respective surfaces of prosthesis 20.

At least one of nonarticulating surfaces 26, 28, and 30 may include pockets or depressions 38 formed therein. Pockets 38 may receive cement to facilitate initial fixation of prosthesis 20 or allow for placement of porous materials therein to facilitate osseointegration of bone or cartilage into prosthesis 20. Pockets 38 advantageously are configured to contain cement or porous material placed therein, thereby enhancing fixation and fatigue resistance of prosthesis 20. Pockets 38 may be self-contained, i.e., surfaces 26, 28, or 30 act as rails or walls to substantially surround pockets 38 such that any material placed in pockets 38 is maintained in pockets 38 when prosthesis 20 is secured to femur 21.

Referring now to FIG. 2, femoral trochlea prosthesis 50 is conceptually shown and may be implantable on distal femur 58. In a dysplastic condition as shown in FIG. 2, distal femur 58 may have less bone on medial condyle 60 as compared to lateral condyle 62, or vice versa. To accommodate such a dysplastic condition, prosthesis 50 may be used. Prosthesis 50 may include articulating surface 52 which may have an asymmetric patella groove angle. Prosthesis 50 may also include nonarticulating surface 54 including some flat surfaces and/or some contoured surfaces. In an exemplary embodiment, prosthesis 50 includes wing or extension 56. Wing 56 may be disposed on a side of prosthesis 50 to match the dysplastic condition of distal femur 58. For example, as shown in FIG. 2, wing 56 is disposed as a projecting portion on the medial side of prosthesis 50 to compensate for the dysplastic condition of medial condyle 60. The projecting portion of prosthesis 50 defined by wing 56 forces the medial condyle of prosthesis 50 anteriorly away from femur 58 to more closely replicate a normal anatomical condition. Wing 56 may define a pocket between prosthesis 50 and distal femur 58 to facilitate containment of cement or porous material disposed between nonarticulating surface 52 and distal femur 58. Wing 56 extends from nonarticulating surface 52 of prosthesis 50 to physically contact medial condyle 60, thereby enhancing support for prosthesis 50 when used with a dysplastic femur 58. Advantageously, prosthesis 50 may account for variable femoral anatomy while facilitating minimal or no bone resection prior to implantation and ensuring good fixation and support of prosthesis 50 in distal femur 58. When prosthesis 50 is implanted, wing 56 of prosthesis 50 advantageously contacts distal femur 58, thereby providing a pocket for containing cement and porous material disposed between nonarticulating surface 52 and femur 58 as well as reducing the potential of soft tissue impingement on the edge of prosthesis 50. In another embodiment, wing 56 may extend around the entire perimeter defined by nonarticulating surface 52 of prosthesis 50. In an exemplary embodiment, wing 56 may be confined to certain desired locations on prosthesis 50.

Figure 3A:
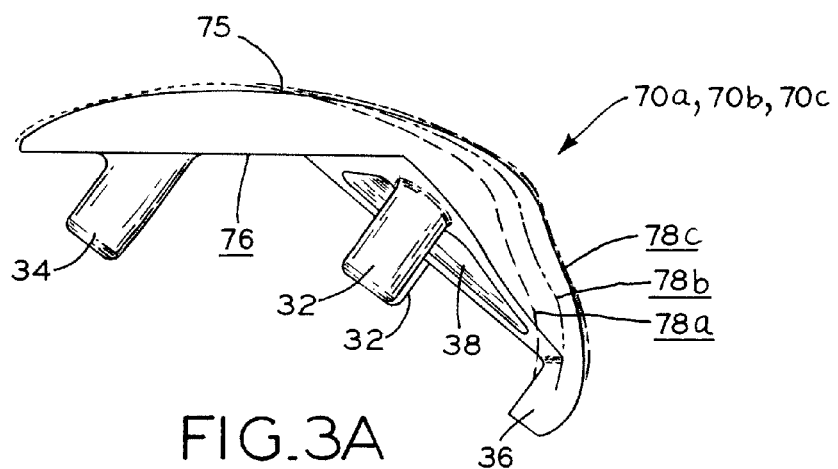
FIG. 3A is a side view of exemplary femoral trochlea prostheses according to yet another embodiment of the present disclosure.
Figure 3B:
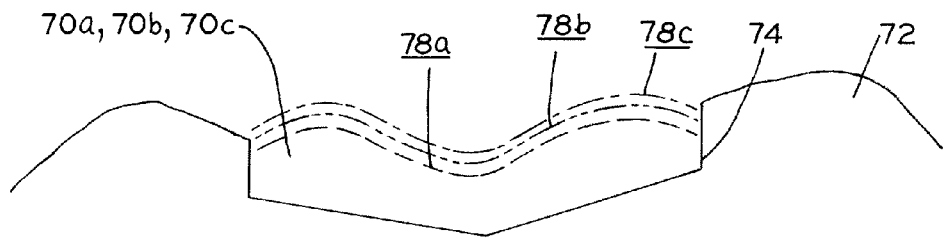
FIG. 3B is a proximal view of a portion of a distal femur with the various prostheses of FIG. 3A implanted therein.

Referring now to FIGS. 3A and 3B, a set of prostheses including femoral trochlea prostheses 70a, 70b, and 70c each may include anterior articulating surface 75, anterior nonarticulating surface 76, a plurality of bone or fixation pegs 32, 34, distal tail 36, and pockets 38, as described above with reference to FIGS. 1A, 1B, and 1C. Prosthesis 70a includes distal articulating surface 78a, prosthesis 70b includes distal articulating surface 78b, and prosthesis 70c includes distal articulating surface 78c. As shown in FIGS. 3A and 3B, articulating surfaces 78a, 78b, and 78c define three different thicknesses of distal articulating surface 78 of each prosthesis 70, for example. Although the set of prostheses is shown as including only three prostheses 70a, 70b, 70c, more prostheses 70 may be provided in the set of prostheses. Each prosthesis 70a, 70b, and 70c is implantable in resected portion 74 of distal femur 72, as shown in FIG. 3B. Advantageously, the set of prostheses 70 defined by prostheses 70a, 70b, and 70c provide a plurality of choices for thickness of distal articulating surface 78 once resected portion 74 has been completed. The surgeon can choose the best fitting prosthesis to match the resected anatomy of distal femur 72. Advantageously, the surgeon can intraoperatively adjust the fit of a prosthesis 70 while simultaneously maintaining the most bone-conserving approach because the surgeon is not required to further resect distal femur 72 to provide the best fit. The surgeon can instead select a prosthesis 70 which will provide the greatest probability of a smooth transition with the patella when transitioning between flexion and extension. In an exemplary embodiment, the distal thicknesses of prostheses 70a, 70b, and 70c may differ by approximately 1 to 2 mm, for example. In alternative embodiments, the distal thicknesses may differ by smaller or larger increments than 1 to 2 mm. In one embodiment, a plurality of augments of varying thicknesses may be utilized with prostheses 70a, 70b, and 70c to further enhance the transition and fit of prosthesis 70 and to accommodate for potential dysplastic conditions on distal femur 72.

Referring to FIG. 4, femoral trochlea prosthesis 90 may be implantable in distal femur 96. Prosthesis 90 may include a plurality of bone pegs 32 and distal tail 36, as described above with reference to FIGS. 1A, 1B, and 1C. Distal femur 96 may include resected portions 98 and 100 for receipt of bone pegs 32 and distal tail 36, respectively. Prosthesis 90 includes articulating surface 92 which defines perimeter 94 therearound. Porous medium 102 may be positioned near perimeter 94 and on any other surfaces of prosthesis 90 which are proximate to bone or cartilage after implantation of prosthesis 90, e.g., distal tail 36, bone pegs 32, and the nonarticulating surface of prosthesis 90. Porous medium 102 may be formed as an inlay around perimeter 94 and may include cartilage and/or bone ingrowth/regrowth media or scaffolding. Porous medium 102 may promote cartilage and/or bone ingrowth for long-term stability of adjacent cartilage and bone at intersections between the cartilage and/or bone and prosthesis 90. Medium 102 may be formed as, but not limited to, materials such as collagen scaffold, as a bioresorbable beta-chitin sponge, as a polymer scaffold, as an open-cell porous metal such as a material made using Trabecular Metal™ technology, available from Zimmer, Inc. of Warsaw, Ind., as fibrous metal, or as material made using Cancellous-Structured Titanium™ (CSTi™) technology, available from Zimmer, Inc. of Warsaw, Ind., for example.

Although described in FIG. 4 and above as a femoral trochlea prosthesis, prosthesis 90 may be any orthopaedic implant, such as a patella, tibial component, a shoulder component, or a hip component, for example, which may include porous medium 102 positioned near a perimeter 94 thereof.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A femoral trochlea prosthesis for implantation in a distal femur of a knee joint, the prosthesis articulating with a patellar component of the knee joint, the prosthesis comprising:
   an articulating surface;
   a nonarticulating surface, said nonarticulating surface defining at least one anterior nonarticulating surface and at least one distal nonarticulating surface; and
   at least one fixation support extending proximally from said distal nonarticulating surface proximate a distal most region of the prosthesis, said fixation support extending in a direction substantially perpendicular to said at least one distal nonarticulating surface and in a direction nonparallel and non-perpendicular with said anterior nonarticulating surface, said articulating surface transitioning smoothly in a posterior direction into said fixation support proximally of said distal nonarticulating surface.

2. The femoral trochlea prosthesis of claim 1, wherein said fixation support is disposed at a distal most and a posterior most portion of the prosthesis.

3. The femoral trochlea prosthesis of claim 1, wherein said at least one fixation support includes a porous medium.

4. The femoral trochlea prosthesis of claim 1, further comprising a plurality of bone peg fixation devices disposed on said nonarticulating surface.

5. The femoral trochlea prosthesis of claim 1, further comprising at least one containment device formed in said nonarticulating surface.

6. The femoral trochlea prosthesis of claim 1, wherein said nonarticulating surface defines a perimeter, the prosthesis further comprising an extension portion extending from said nonarticulating surface substantially along said perimeter.

7. The femoral trochlea prosthesis of claim 1, whereby, with said distal nonarticulating surface positioned against a prepared surface of the distal femur, said fixation support is surrounded by bone located proximally of at least a portion of the prepared surface of the distal femur.

8. The femoral trochlea prosthesis of claim 1, wherein said articulating surface transitions smoothly into said fixation support to define a transition region, and whereby, with said nonarticulating surface positioned against the femur, said transition region borders a non-resected surface of the distal femur.

9. The femoral trochlea prosthesis of claim 1, wherein said distal nonarticulating surface extends obtusely from said anterior nonarticulating surface.

10. The femoral trochlea prosthesis of claim 1, wherein said anterior nonarticulating surface and said fixation support define an acute angle therebetween.

11. The femoral trochlea prosthesis of claim 4, wherein said plurality of bone peg fixation devices extend substantially parallel to said fixation support.

12. The femoral trochlea prosthesis of claim 4, wherein a diameter of said plurality of bone peg fixation devices is substantially equal to a width of said fixation support.

13. The femoral trochlea prosthesis of claim 4, wherein said plurality of bone peg fixation devices and said fixation support extend a substantially equal distance from said nonarticulating surface.

* * * * *